United States Patent [19]
Kurz et al.

[11] Patent Number: 5,514,177
[45] Date of Patent: May 7, 1996

[54] EAR OSSICLE PROSTHESIS FOR SOUND TRANSMISSION IN NEEDLE TUBE, WITH A POST COMPOSED OF PURE GOLD

[76] Inventors: Heinz Kurz, Tübinger Strasse 3, D-72144 Dusslingen; Dietrich Plester, Lichtenbergerweg, D-72070, Tuübingen, both of Germany

[21] Appl. No.: 208,602

[22] Filed: Mar. 9, 1994

[51] Int. Cl.$^6$ .................................. A61F 2/18
[52] U.S. Cl. ............................. 623/10; 623/11
[58] Field of Search ................. 623/10, 11, 16, 623/66

[56] References Cited

U.S. PATENT DOCUMENTS

| | | |
|---|---|---|
| 3,838,468 | 10/1974 | Armstrong . |
| 3,909,852 | 10/1975 | Homsy . |
| 4,287,616 | 9/1981 | Heimke et al. ............... 623/10 |
| 4,510,627 | 4/1985 | Treace et al. . |
| 4,655,776 | 4/1987 | Lesinski . |
| 5,061,280 | 10/1991 | Prescott . |
| 5,104,401 | 4/1992 | Kurz ............................. 623/10 |

FOREIGN PATENT DOCUMENTS

| | | |
|---|---|---|
| 0563767 | 10/1993 | European Pat. Off. ........... 623/10 |
| 3211209 | 11/1983 | Germany . |
| 3901796 | 7/1990 | Germany . |
| 3722410 | of 1992 | Germany . |
| 0619182 | 8/1978 | U.S.S.R. ............................ 623/10 |

*Primary Examiner*—Randall L. Green
*Assistant Examiner*—P. Zuttarelli
*Attorney, Agent, or Firm*—Michael J. Striker

[57] ABSTRACT

An ear ossicle prosthesis for sound transmission in a middle tube comprises a post composed of a gold and having two ends and a coupling body composed of pure titanium and coupled with at least one of the ends of the pure gold post.

10 Claims, 1 Drawing Sheet

5,514,177

EAR OSSICLE PROSTHESIS FOR SOUND TRANSMISSION IN NEEDLE TUBE, WITH A POST COMPOSED OF PURE GOLD

BACKGROUND OF THE INVENTION

The present invention relates to an ear ossicle prosthesis for sound transmission in needle tube, with a post composed of pure gold.

Ear ossicle prostheses made from pure gold and implanted in ears have been recommended in view of their compatibility and their sound transmission property. When these prostheses are placed however directly on the ear drum of a patient, there is substantial disadvantage in the instability of the ear drum, so that the prostheses can change their position on the ear drum and diffuse in the ear drum. It was recommended to anchor the ear ossicle prostheses at the side of the ear drum on the frequently available hammer piece. However, the material property of a fine steel prosthesis makes its mounting difficult.

SUMMARY OF THE INVENTION

Accordingly, it is an object of the present invention to provide an ear ossicle prosthesis of the above mentioned type, with which a good anchoring on the ear organs is obtained.

In keeping with these objects and with others which will become apparent hereinafter, one feature of the present invention resides, briefly stated, in an ear ossicle prosthesis in which at least one post end of the prosthesis is connected with a coupling body composed of pure titanium.

Parts of pure titanium are covered under the action of oxygen with a relatively rough oxide layer. It has been determined that this oxide layer is very well body compatible or in other words it does not provoke inflammations during contact with the skin and with bone parts. The rough surface of the titanium oxide layer facilitates for the prosthesis part a good seat on a bone or cartilage part and provides for the possibility for the bone substance and the cartilage substance to grow into the depressions of the surface of the prosthesis part and thereby to additionally insure the connection with the prosthesis. By special welding processes a good and firm connection between the part composed of the pure gold and a part of the prosthesis composed of pure titanium is provided.

The shape of the ear ossicle prosthesis and in particular its parts arranged on both ends of the prosthesis post can be designed differently, depending onto which degree the ear ossicle must be replaced. In a full prosthesis between the ear drum and the foot plate of the stirrup it is advantageous to provide at one end of the wire shaped pure gold post a hook part which is composed of pure titanium and is placeable on a hammer grip residual portion on the ear drum, while on another end of the pure gold post a full prosthesis of a slotted bell body also composed of pure titanium can be placed to abut against the foot plate.

In the cases in which the stirrup is substantially obtained, on the end of the pure gold post also a slotted bell body composed of pure gold can be arranged, while on the other end of the pure gold post a slotted collar of pure titanium can be arranged for extension on the anvil leg or on the hammer grip.

For reliable anchoring of the ear ossicle prosthesis during the operation, the bell body arranged on one end of the prosthesis post can be advantageously slotted in a cross-shaped manner and thereby facilitate a change of the bell edge diameter.

Also, the collar produced from both titanium can advantageously be slotted many times and preferably composed of a longitudinally slotted titanium collar which for improving its deformability is provided at least at one location with a partial transverse slot.

Preferably, the post composed of pure gold is provided with at least one angling, flexing or bending.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
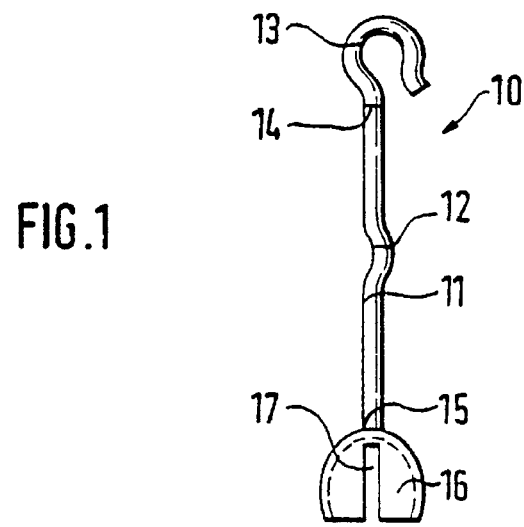
FIG. 1 is a schematic side view of a full ear ossicle prosthesis in accordance with the present invention.

A full prosthesis shown in FIG. 1 has a post 11 which is hammered of a pure gold wire and has in its central region a curve 12 permitting a length change. On the upper end of the post 11 in FIG. 1 a hook part 13 composed of pure titanium is connected in a butt joint by a laser weld point 14. At the other lower end in FIG. 1 the post 11 composed of pure gold is connected with a bell body 16 by a weld point 15. The bell body 16 is slotted in a crossing manner for changing of its diameter. In the drawing a crossing slot 13 extending perpendicular to the plane of the drawing is illustrated. The other crossing slot extends, as not shown in the drawings, in the plane of the drawing. The hook part 13 serves for anchoring of the full prosthesis 10 on a hammer grip residual part on the ear drum of a patient. The bell body 16 serves for abutment of the full prosthesis 10 against the foot plate of a patient with no longer available stirrup and anvil.

Figure 2:
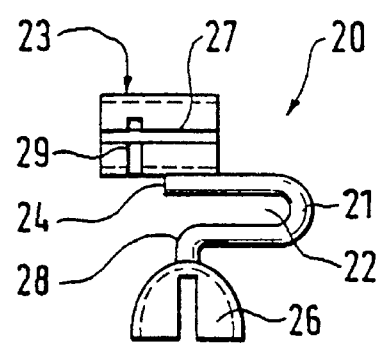
FIG. 2 is a side view of the first embodiment of a partial ear ossicle prosthesis in accordance with the present invention.

A partial prosthesis 20 shown in FIG. 2 has a post 21 hammered from a fine gold wire and bent laterally to form a U-shape. A coupling body composed of a pure titanium and formed as a collar 23 is mounted on the end of leg by a welding point 24. A bell body 26 is mounted on the other leg of the post 21 which ends in a band 28 or just formed on it. Its shape at least approximately corresponds to the shape of the bell body 16 on FIG. 1, but here is composed of pure gold. The slotted bell body 26 is formed for anchoring of the partial prosthesis 20 on the stirrup body. The titanium collar 23 which is composed of a titanium bushing having a longitudinal slot 27 and an additional partial transverse slot 29, performs anchoring of the partial prosthesis 20 on the hammer grip.

Figure 3:
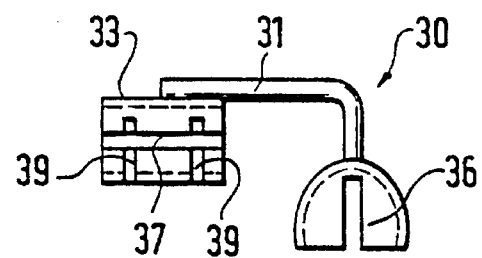
FIG. 3 is a side view of a second embodiment of a partial ear ossicle prosthesis of the invention.

FIG. 3 shows a partial prosthesis 30 in which a collar composed of a pure titanium is mounted on one end of a prosthesis post 31 which is bent by 90° and composed of pure gold. The titanium collar, similarly to the collar 23 of FIG. 2 is formed as a titanium bushing provided with a throughgoing longitudinal slot 37 and additionally with partial transverse slots 39 for facilitating its deformation. The partial transverse slots 39 extend substantially over ⅔ of the bush periphery. A bell body 36 composed of pure gold and slotted in a crossing manner is mounted or formed on the second end of the post 31. The partial prosthesis 30 is provided for anchoring with its bell body 36 on a stirrup and for anchoring with its titanium collar 33 on an anvil leg.

It will be understood that each of the elements described above, or two or more together, may also find a useful application in other types of constructions differing from the types described above.

While the invention has been illustrated and described as embodied in an ear ossicle prosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An ear ossicle prosthesis for sound transmission in a middle tube, comprising a post composed of gold and having two ends; and a coupling body composed of pure titanium and coupled with at least one of said ends of said pure gold post, said pure gold post having at least one bending.

2. An ear ossicle prosthesis for sound transmission in a middle tube, comprising a post composed of gold and having two ends; and a coupling body composed of pure titanium and coupled with at least one of said ends of said pure gold post.

3. An ear ossicle prosthesis as defined in claim 1; and further comprising a slotted bell body composed of pure gold and arranged on one of said ends of said pure gold post for extension on a stirrup, said coupling member including a slotted collar composed of pure titanium and arranged on the other end of said pure gold post for extension on an anvil leg or a hammer grip for providing a partial prosthesis between the stirrup and the anvil leg or the hammer grip.

4. An ear ossicle prosthesis as defined in claim 1; and further comprising means for connecting said at least one coupling body to said pure gold post and including a welding seam.

5. An ear ossicle prosthesis as defined in claim 1, wherein said pure gold post has at least one angling.

6. An ear ossicle prosthesis as defined in claim 1, wherein said pure gold post has at least one flexing.

7. An ear ossicle prosthesis as defined in claim 1; and further comprising a bell body arranged at one of said ends of said pole and slotted in a crossing manner for changing a bell diameter.

8. An ear ossicle prosthesis as defined in claim 1, wherein said coupling body is a collar which is formed as a longitudinally slotted titanium bushing, said titanium bushing being provided at least at one point additionally with a partial transverse slot for improving its deformability.

9. An ear ossicle prosthesis for sound transmission in a middle tube, comprising a post composed of gold and having two ends; and a coupling body composed of pure titanium and coupled with at least one of said ends of said pure gold post, said pure gold post being wire shaped, said coupling body including a hook part composed of pure titanium and arranged on one of said ends of said pure gold post so as to be placeable on a hammer grip procedural part on an ear drum, and a slotted bell body composed of pure titanium and arranged on the other side of said pure gold post for abutment against a foot plate of a stirrup, so as to form a full prosthesis between the ear drum and the foot plate.

10. An ear ossicle prosthesis for sound transmission in a middle tube, comprising a post composed of gold and having two ends; and a coupling body composed of pure titanium and coupled with at least one of said ends of said pure gold post, said pure gold post being wire shaped, said coupling body including a hook part composed of pure titanium and arranged on one of said ends of said pure gold post so as to be placeable on a hammer grip procedural part on an ear drum, and a slotted bell body composed of pure titanium and arranged on the other side of said pure gold post for abutment against a foot plate of a stirrup, so as to form a full prosthesis between the ear drum and the foot plate, said pure gold post having at least one bending.

* * * * *